United States Patent [19]

Eubanks et al.

[11] Patent Number: 4,605,521

[45] Date of Patent: Aug. 12, 1986

[54] PROCESS FOR THE PREPARATION OF ORGANIC NITRILES FROM ORGANIC CARBOXYLIC ACID PRIMARY AMIDES

[75] Inventors: Robert J. I. Eubanks; James G. Pacifici, both of Batesville, Ark.

[73] Assignee: Eastman Kodak Company, Rochester, N.Y.

[21] Appl. No.: 717,926

[22] Filed: Mar. 29, 1985

[51] Int. Cl.$^4$ ............................................. C07C 120/10
[52] U.S. Cl. ..................................... 558/313; 546/286
[58] Field of Search ................. 260/465 B, 465.2, 464; 546/286

[56] References Cited

U.S. PATENT DOCUMENTS 3,317,585  5/1967  Herschmann ................... 260/465.2

Primary Examiner—Dolph H. Torrence
Attorney, Agent, or Firm—Clyde L. Tootle; J. Frederick Thomsen

[57] ABSTRACT

This invention relates to a process for the preparation of organic nitriles. More particularly, the invention relates to a process for the preparation of organic nitriles by reacting organic carboxylic acid primary amides with a dehydrating agent in the presence of a catalytic amount of a particular quaternary ammonium salt.

12 Claims, No Drawings

PROCESS FOR THE PREPARATION OF ORGANIC NITRILES FROM ORGANIC CARBOXYLIC ACID PRIMARY AMIDES

DESCRIPTION

This invention relates to a process for the preparation of organic nitriles. More particularly, the invention relates to a process for the preparation of organic nitriles by reacting organic carboxylic acid primary amides with a dehydrating agent in the presence of a catalytic amount of a particular quaternary ammonium salt.

The organic nitriles are used in many organic synthesis processes. Such compounds have been well known in the art for many years. Such organic nitriles can be prepared by reacting an aliphatic, cycloaliphatic or aromatic carboxylic acid primary amide with a dehydrating agent such as thionyl chloride. Other dehydrating agents are known in the art such as, for example, phosphorous pentoxide, acetic anhydride and the like. Generally, the preferred dehydrating agent is thionyl chloride since it can be easily handled and forms gaseous by products, hydrogen chloride and sulfur dioxide, which allows relatively simple workups. The use of thionyl chloride however in many reactions reacts slowly, requires long reaction times, elevated reaction temperatures and large excesses of thionyl chloride for dehydration reactions. The use of large excesses of thionyl chloride in dehydration reactions is undesirable since any unreacted thionyl chloride must be removed before the product is isolated and recovered. In addition, the use of an excess amount of thionyl chloride in combination with high reaction temperatures and long stripping times at temperatures greater than 60° C. will rapidly darken organic nitriles and increase residual sulfur content which is also undesirable.

In an attempt to eliminate or reduce the above undesirable aspects, catalysts such as N,N-dimethylformamide (DMF) have been widely used in preparing a variety of organic nitriles. The DMF catalyst provides dehydration reactions at shorter reaction times, at lower temperatures and with a less amount of thionyl chloride. However, relatively large amounts of DMF are necessary. Moreover, when DMF is exposed to thionyl chloride and other such dehydration agents such as phosphorous pentoxide and the like, there is formed N,N-dimethylcarbamoyl chloride (DMCC) which is a proven carcinogen in mice and a possible carcinogen in humans. Therefore, when dehydration processes are carried out where DMCC may be produced there are procedures which must be carried out to ensure that there is no human exposure in the work place to the DMCC. Therefore, dehydration processes where DMF is present and could form DMCC during the dehydration which could result in human exposure to such formed DMCC are highly undesirable.

Therefore, it would be an advance in the state of the art to provide a dehydration process to prepare organic nitriles in high yields and efficiency where DMCC was not formed in the dehydration process and only a small amount of catalyst is required.

In accordance with the present invention, it has been found that the use of a quaternary ammonium salt as a catalyst in the dehydration of organic carboxylic acid primary amides to form organic nitriles provides a highly efficient and safe dehydration process.

The quaternary ammonium salt used in a catalytic amount has the formula:

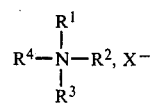

wherein
$R^1$, $R^2$, $R^3$, and $R^4$ are each independently selected from alkyl of from 1 to 18 carbon atoms, alkylaryl of from 7 to 18 carbon atoms, arylalkyl of from 7 to 18 carbon atoms, and aryl of from 6 to 18 carbon atoms and X is an anion such as hydroxyl, halogen, hydrogen sulfate, perchlorate, hydroxide anion and the like. The quaternary ammonium salts in which $R_1$, $R_2$ and $R_3$ each independently contain 1 to 4 carbon atoms and $R_4$ contains 1 to 4 carbon atoms or a benzyl group are preferred. Such preferred quaternary ammonium salts include tetraethylammonium chloride, tetraethylammonium bromide, tetraethylammonium hydroxide, benzyltriethylammonium chloride, benzyltriethylammonium hydroxide, benzyltriethylammonium bromide, and ethyltrimethylammonium chloride, ethyltrimethylammonium hydroxide, propyltrimethylammonium hydroxide, butyltrimethylammonium hydroxide, tetraethylammonium bromide, tetrabutylammonium bromide, tetrabutylammonium hydroxide, tetraethylammonium acetate, and mixtures thereof. Such salts are disclosed as being useful as catalysts in heterogeneous reactions in U.S. Pat. No. 3,992,432.

The quaternary ammonium salts of this process generally are employed in a catalytic amount, that is, any amount which exhibits a favorable comparison in the reaction as compared to the use of the dehydrating agent alone. Typically this amount will be about 0.01 mol percent to about 0.1 mol percent of the organic acid primary amide reactant, preferably 0.02 to 0.05 mol percent, most preferably about 0.03 mol percent.

Suitable organic carboxylic acid primary amides useful in the present invention can be aliphatic, cycloaliphatic, heterocyclic or aromatic carboxylic acid primary amides. The aliphatic carboxylic acid primary amides can be straight or branched chain acid primary amides containing 2 to 22 carbon atoms. The organic carboxylic acid primary amides such as the longer chain length or high molecular weight are generally slower reacting than the short chain aliphatic acid primary amides. The aliphatic, cycloaliphatic, heterocyclic, and aromatic carboxylic acid primary amides can be substituted or unsubstituted. Substituents include any substituent which does not hinder the dehydration, block the dehydration or which react more easily with the carboxyl primary amide group thereby preventing formation of the organic nitrile. Suitable substituents include, for example, alkyl groups, phenyl groups, nitro groups, cyano groups, halogens and the like. Examples of such aliphatic, cycloaliphatic, heterocyclic and aromatic carboxylic acid primary amides are acetamide, propanamide, butanamide, isobutanamide, stearamide, benzamide, pentamide, 3-methylbutamide, hexanamide, heptamide, octamide, nonamide, decamide, undecamide, dodecamide, tetradecamide, hexadecamide, heptadecamide, octadecamide, eicosanoic acid amide, cyclopropanecarboxylic acid amide, cyclopentanecarboxylic acid amide, cyclohexanecarboxylic acid amide, benzamide, p-toluic acid amide, m-toluic acid amide, 1-naphthalene carboxylic acid amide, phenyl acetic acid amide, p-chlorobenzoic acid amide, p-nitrobenzoic acid amide, m-nitrobenzoic acid amide, p-methylbenzoic acid amide, p-methoxybenzoic acid amide, 3,4-dimethoxybenzoic acid amide, nicotinamide and the like.

The dehydration reaction can be carried out in the presence or absence of a solvent depending on the reactants employed. The process is a homogeneous process. Generally the organic carboxylic acid amide used in the present invention are liquids and are miscible with the dehydrating agents, such as thionyl chloride, and the quaternary ammonium salt. It may be desirable in dehydrating the organic carboxylic acid primary amides which have high melting points to carry out the dehydration in non-polar organic solvents such as heptane, hexane, benzene, toluene and the like. The solvent after dehydration can, if desired, be recovered by conventional stripping methods.

Suitable dehydration agents include phosgene, oxaloyl chloride, oxaloyl bromide, oxaloyl iodide, phosphorous trichloride, phosphorous tribromide, phosphorous triiodide, thionyl chloride, thionyl bromide, thionyl iodide, phosphorous pentachloride, phosphorous oxychloride and the like. The preferred dehydration agent is thionyl chloride due to its ease of handling and use.

Stoichiometric quantities of organic acid primary amide and dehydrating agent are employed. If desired, a slight excess of dehydrating agent may be employed, generally up to about 10 mol %, preferably about 5 mol %.

The dehydration is carried out at temperatures generally in the range of about 25° C. to 90° C., preferably about 50° C. to 60° C.

The dehydration can be carried out at atmospheric pressure and may advantageously be conducted under a nitrogen sweep. This effectively allows degassing of strong acid such as HCl, in the case of thionyl chloride, generated in the process which may aid in the formation of unwanted by-products.

The process of this invention can be carried out by adding the dehydrating agent to a homogeneous reaction mixture of the organic carboxylic acid primary amide and quaternary ammonium salt. Equally good results may be achieved by adding the organic carboxylic acid primary amide to a homogeneous reaction mixture of dehydrating agent and the catalyst. The rate of addition of dehydrating agent can be widely varied but generally should be a sufficient rate to utilize the dehydrating agent efficiently. On a laboratory scale, such as disclosed in the experimental examples set out hereinbelow, addition of thionyl chloride was complete in about one hour. Of course, the time can be expected to vary depending on the size of the reaction, the reaction conditions, the reactants, the equipment used, and the like. During the addition of the thionyl chloride in the examples which follow water, hydrogen chloride and sulfur dioxide gases are evolved, thereby minimizing harsh strong acid reaction conditions. After addition of the thionyl chloride the reaction mixture is held at the same temperature (25° C.–90° C.) for a period of time sufficient to ensure completion of the reaction. About 0.25 to 1.0 hour on a small laboratory scale normally is sufficient. Any unreacted thionyl chloride and water which may be present is then removed, i.e., by vacuum distillation, and the product readily isolated by cooling the reaction mixture to room temperature. The resulting product is obtained in good yield (up to about 95%) and high purity which can be used without further purification.

The process of this invention therefore provides the desired organic nitrile product in good yield and purity without the use of long reaction times, large excesses of dehydrating agent, elevated reaction temperatures or the preparation of possibly carcinogens.

The novel process of the present invention therefore provides organic nitriles which are useful as intermediates in the synthesis of organic compounds and other useful materials in a unique and efficient manner.

The invention will be further illustrated by the following Examples although it will be understood that these Examples are included merely for purposes of illustration and are not intended to limit the scope of the invention.

EXAMPLE 1

A homogeneous mixture of benzamide (1.0 mol) and benzyltriethylammonium chloride (0.02 mol percent) was heated to and maintained at 60° to 65° C. while thionyl chloride (1.1 mol) was added over a one-hour period. After the addition was completed, the batch was held at 60° C. to 65° C. for one hour. Unreacted thionyl chloride and water was removed by distillation at reduced pressure (ca 200 mm) to a pot temperature of 85° to 90° C. The product was cooled to room temperature and stored. Approximately 93.7 grams of a clear, pale yellow liquid was isolated which assayed 95.6 percent by GC (0.474 mol, 95 percent of theory). The IR and NMR (H) matched those of benzonitrile.

Similar results can be obtained using thionyl bromide or thionyl iodide in place of thionyl chloride.

EXAMPLE 2

Example 1 was repeated except that stearamide (1.0 mol) was substituted for benzamide. Approximately 95% of the stearamide was converted to stearonitrile.

EXAMPLE 3

Example 2 was repeated except that the benzyltriethylammonium chloride was deleted and the reaction was maintained at reflux for four hours. Approximately 80 percent of the stearamide was converted to stearyl nitrile.

This Example shows that without the quaternary ammonium salt and maintaining the reaction for four hours gave a conversion of only 80% of the stearamide to the corresponding stearyl nitrile as compared to approximately 95% with the quaternary ammonium salt.

EXAMPLE 4

Example 3 was repeated except that N,N-dimethylformamide (DMF) (0.2 mol) was added to the stearamide as a catalyst in place of the quaternary ammonium salt and the reaction maintained for one hour. Approximately 90 percent of the stearamide was converted to the stearyl nitrile.

This Example shows that with a conventional dehydration catalyst, DMF, in an amount ten times greater than the amount of the quaternary ammonium salt used in Example 2, provided a conversion of only about 90 percent whereas with only a tenth the amount of the quaternary ammonium salt of Example 2 provided about a 95 percent conversion.

EXAMPLE 5

Example 2 was repeated except that butamide was used in place of stearamide. Similar results were obtained with a conversion of about 95 percent of the butamide to butyl nitrile.

Similar results were obtained substituting propylamide, pentamide, hexamide and octamide for butamide.

EXAMPLE 6

Example 5 was repeated except that dodecamide was substituted for butamide. Similar results were obtained with a conversion of about 95 percent of the dodecamide to dodecanyl nitrile.

Similar results are obtained when octamide, nonamide, decamide, undecamide, tetradecamide, pentadecamide, hexadecamide, heptadecamide, octadecamide and nonadecamide were substituted for dodecamide.

EXAMPLE 7

Example 2 was repeated except that cyclohexamide was substituted for stearamide. Similar results were obtained with a conversion of about 95 percent of the cyclohexamide to cyclohexyl nitrile.

Similar results were obtained when 4-methyl cyclohexamide, 4-chlorocyclohexamide and 3,4,5-trichlorocyclohexamide were substituted for cyclohexamide.

EXAMPLE 8

Example 2 was repeated except that the amount of benzyltriethylammonium chloride was reduced to 0.01 mol percent. Similar results were obtained but the amount of stearamide converted was only about 88 percent. Extending the reaction time to two hours gave a conversion of about 95 percent.

Repeating this Example increasing the amount of catalyst to 0.1 mol percent converted about 95 percent of the stearamide in about one hour.

This Example shows that with only 0.01 percent catalyst the process provides good conversions of the organic carboxylic acid primary amide to the organic nitrile under acceptable conversion rates. Increasing the amount of catalyst greater than 0.1 percent only used more catalyst than necessary with no detectable increase in conversion rates.

The present process provides an effective and cost efficient process for the preparation of organic nitriles in good conversion rates and good yields.

The invention has been described in detail with particular reference to preferred embodiments thereof, but it will be understood that variations and modifications can be effected within the spirit of the invention.

We claim:

1. A homogeneous process for preparing organic nitriles which comprises reacting an organic carboxylic acid primary amide selected from the group consisting of aliphatic carboxylic acid primary amide, cycloaliphatic carboxylic acid primary amide, heterocyclic carboxylic acid primary amide and aromatic carboxylic acid primary amide containing about 2 to about 22 carbon atoms with at least a stoichimetric amount of a dehydrating agent at a tenperature of about 25° C. to 90° C. in the presence of a catalytic amount of a quaternary ammonium salt having the formula:

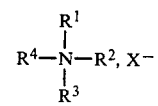

wherein
$R^1$, $R^2$, $R^3$, and $R^4$ are each independently selected from alkyl of from 1 to 18 carbon atoms, alkylaryl of from 7 to 18 carbon atoms, arylalkyl of from 7 to 18 carbon atoms, and aryl of from 6 to 18 carbon atoms and X is an anion.

2. A process according to claim 1 wherein said dehydrating agent is thionyl chloride.

3. A process according to claim 2 wherein said quaternary ammonium salt is benzyltriethylammonium chloride.

4. A process according to claim 2 wherein said organic carboxylic acid primary amide is an aromatic carboxylic acid primary amide containing about 7 to about 22 carbon atoms.

5. A process according to claim 4 wherein said aromatic carboxylic acid primary amide is substituted or unsubstituted benzamide.

6. A process according to claim 5 wherein said substituted or unsubstituted benzamide is benzamide.

7. A homogeneous process for preparing organic nitriles which comprises reacting an organic carboxylic acid primary amide selected from the group consisting of aliphatic carboxylic acid primary amide, cycloaliphatic carboxylic acid primary amide, heterocyclic carboxylic acid primary amide and aromatic carboxylic acid primary amide containing about 2 to about 22 carbon atoms with at least a stoichiometric amount of a dehydrating agent at a temperature of about 25° C. to 90° C. in the presence of a quaternary ammonium salt having the formula

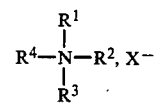

wherein
$R^1$, $R^2$, and $R^3$ each independently contain 1 to 4 carbon atoms and $R^4$ contains 1 to 4 carbon atoms or a benzyl group and X is halide, hydrogen sulfate, perchlorate or hydroxide anion.

8. A process according to claim 7 wherein said dehydrating agent is thionyl chloride.

9. A process according to claim 8 wherein said quaternary ammonium salt is benzyltriethylammonium chloride.

10. A process according to claim 9 wherein said organic carboxylic acid primary amide is an aromatic carboxylic acid primary amide containing about 7 to about 22 carbon atoms.

11. A process according to claim 10 wherein said aromatic carboxylic acid primary amide is substituted or unsubstituted benzamide.

12. A process according to claim 11 wherein said substituted or unsubstituted benzamide is benzamide.

* * * * *

UNITED STATES PATENT AND TRADEMARK OFFICE
CERTIFICATE OF CORRECTION

PATENT NO. :   4,605,521

DATED      :   August 12, 1986

INVENTOR(S) :  Robert J. I. Eubanks and James G. Pacifici

It is certified that error appears in the above-identified patent and that said Letters Patent is hereby corrected as shown below:

Column 5, line 66, delete "tenperature" and insert therefor ---temperature---.

Column 6, line 28, delete "benzamide" and insert therefor ---benzyl amide---.

Signed and Sealed this

Ninth Day of December, 1986

Attest:

DONALD J. QUIGG

*Attesting Officer*         *Commissioner of Patents and Trademarks*